United States Patent [19]
Ellman et al.

[11] Patent Number: 5,562,503
[45] Date of Patent: Oct. 8, 1996

[54] BIPOLAR ADAPTOR FOR ELECTROSURGICAL INSTRUMENT

[76] Inventors: Alan G. Ellman; Jon C. Garito, both of 1135 Railroad Ave., Hewlett, N.Y. 11557

[21] Appl. No.: 349,428

[22] Filed: Dec. 5, 1994

[51] Int. Cl.$^6$ ............................ H01R 13/70; A61B 17/39
[52] U.S. Cl. .................... 439/638; 200/51.03; 606/34; 606/42
[58] Field of Search ................. 439/52, 638; 200/51 R, 200/51.02, 51.03, 51.04, 51.05, 51.06, 554; 606/32, 34, 42, 45, 48

[56] References Cited

U.S. PATENT DOCUMENTS 4,244,371 1/1981 Farin ............................................ 606/34
5,342,356 8/1994 Ellman et al. ............................ 606/42

*Primary Examiner*—Neil Abrams

[57] ABSTRACT

An adaptor apparatus configured to plug directly into the connectors on the front panel of an electrosurgical instrument, and provided with connector means for receiving mating connectors of both an unipolar handpiece and a bipolar forceps. Switch means are provided on the adaptor apparatus for allowing a surgeon in an operating room to easily switch over from the unipolar to the bipolar mode by simply throwing the switch. Since the adaptor can be attached to the electrosurgical instrument and the unipolar handpiece and bipolar forceps both attached to the adaptor before a sterile field is created, only the switch handle need be touched to switch between the two modes. Thus, it is easy to maintain the sterile field of the operating room.

10 Claims, 4 Drawing Sheets

5,562,503

BIPOLAR ADAPTOR FOR ELECTROSURGICAL INSTRUMENT

The invention is directed to adaptor apparatus for connection to an electrosurgical instrument or apparatus.

BACKGROUND OF INVENTION

Electrosurgical instruments are well known and widely used in the medical, dental, and veterinarian fields. They offer the capability of precision cutting with electrosurgical currents in the megacycle range using a handpiece with needle, ball, or loop electrodes in a unpolar operating mode, or convenient coagulation using a forceps in a bipolar operating mode. Ellman International, Inc. makes available an electrosurgical instrument which provides on its front panel connectors for receiving the plug of a unipolar handpiece and a ground or indifferent plate, as well as connectors for receiving the plugs of a bipolar forceps.

In a typical surgical setting, a surgeon may first use the unipolar handpiece to perform a desired cutting procedure and then desire to use the bipolar forceps for coagulation of blood vessels because of its unique ability to coagulate in a fluid field. This creates problems in maintaining the requisite sterile field while still allowing the surgeon to unplug and plug in different devices. There is at present no convenient way for the surgeon to do this effectively without jeopardizing the sterile field.

SUMMARY OF INVENTION

The principal object of the invention is means to simplify the maintainence of a sterile field during surgery while changing between unipolar and bipolar modes of an electrosurgical instrument.

A further object of the invention is low-cost apparatus that simplifies the changing between unipolar and bipolar modes of an electrosurgical instrument during surgery.

These objects are achieved in accordance with one aspect of the invention by an adaptor apparatus configured to plug directly into the connectors on the electrosurgical instrument, and provided with connector means for receiving mating connectors of both the unipolar handpiece and the bipolar forceps. Switch means are provided on the adaptor apparatus for allowing the surgeon to easily switch over from the unipolar to the bipolar mode by simply throwing the switch, Since the adaptor can be attached to the electrosurgical instrument and the unipolar handpiece and bipolar forceps both attached to the adaptor before the sterile field is created, only the switch handle need be touched to switch between the two modes, and the switch handle can easily be sterilized. Alternatively, the surgeon can use an elbow to throw the switch without spoiling the sterile field.

The adaptor of the invention offers the advantages of accessibility, immobility, and versatility, providing the surgeon all the benefits of both electrosurgical modes while not jeopardizing the crucial sterile field.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF PREFERRED EMBODIMENTS

Figure 1:
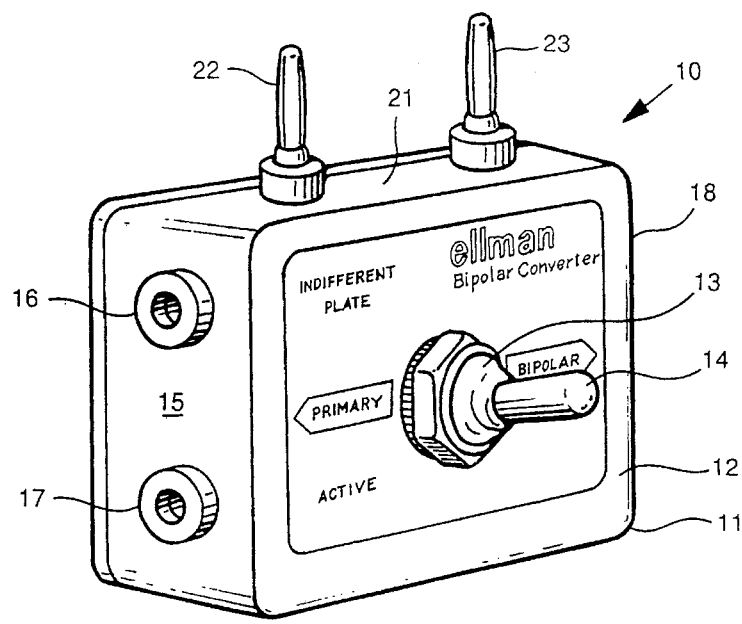
FIG. 1 is a perspective view of one form of adaptor in accordance with the invention.

One form of the adaptor according to the invention is illustrated in FIG.1. The adaptor 10 comprises a box-like housing 11 comprising at the side 12 a power switch 13 with an operating handle 14 protruding forwardly from the housing 11. At the left side 15 are located two female electrical connectors 16, 17, as for example banana female socket connectors. The opposite side 18 contains two similar female socket connectors 19, 20 (not shown in FIG. 1). At the upper side 21 protrude two male connectors 22, 23, as for example banana male plug connectors. Typical housing dimensions are 10–12 cm wide, 2–4 cm deep, and 5–7 cm high in the orientation shown in FIG. 1.

Figure 2:
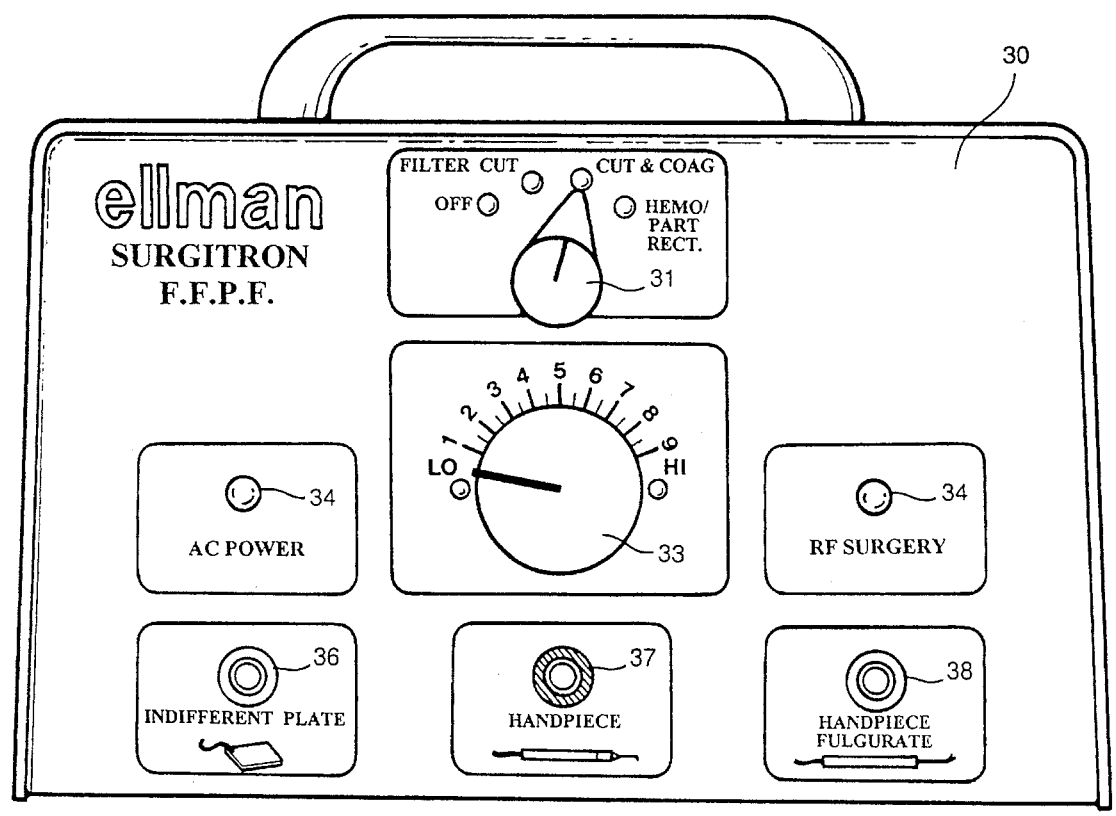
FIG. 2 is a front view of the front panel of a typical electrosurgical instrument.

FIG. 2 shows the front panel of a typical electrosurgical instrument 30, in this instance an Ellman Surgitron machine. It shows a selector switch 31 for desired currents, and a variable power control 33. Two panel indicator lights 34 are present, and below the lights three female connectors 36, 37, and 38, in this instance in the form for example of banana sockets. The labels indicate the functions. The connector 36 at the left is for receiving a plug of the ground plate; the connector 37 at the center is for receiving a plug of a conventional handpiece; and the connector 38 at the right is for receiving a plug of a fulgurate handpiece. For purposes of this invention, only the two connectors 36, 37 are used. The ground plate connector 36 connects internally to the instrument ground, and the handpiece connector 37 connects internally to the power output of the radio-frequency (RF) generator on the inside of the instrument and that supplies the electrosurgical currents to the electrode mounted in the handpiece.

Figure 3:
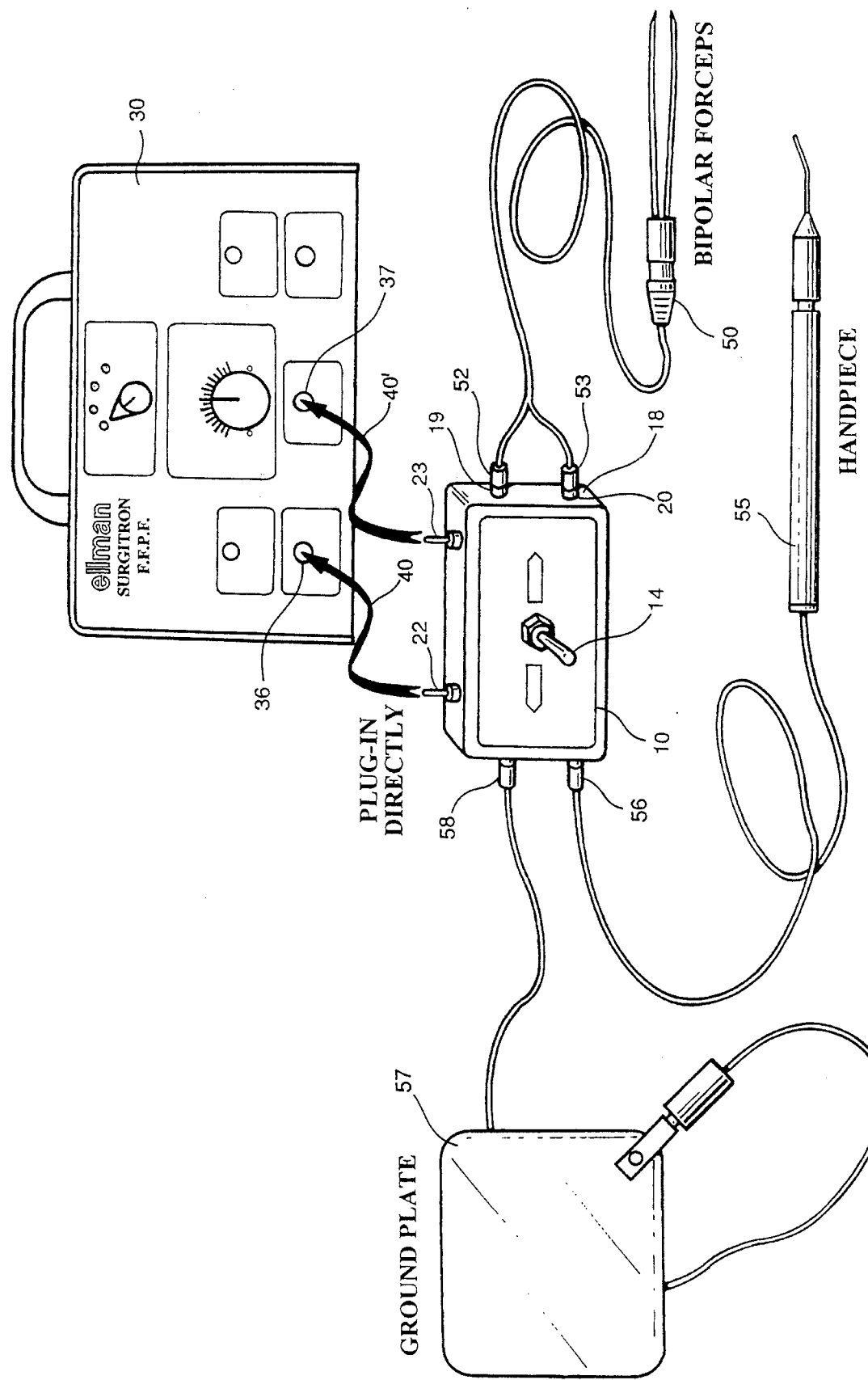
FIG. 3 is schematic view showing how the adaptor of FIG. 1 can plug into the front panel of the instrument of FIG. 2.
Figure 4:
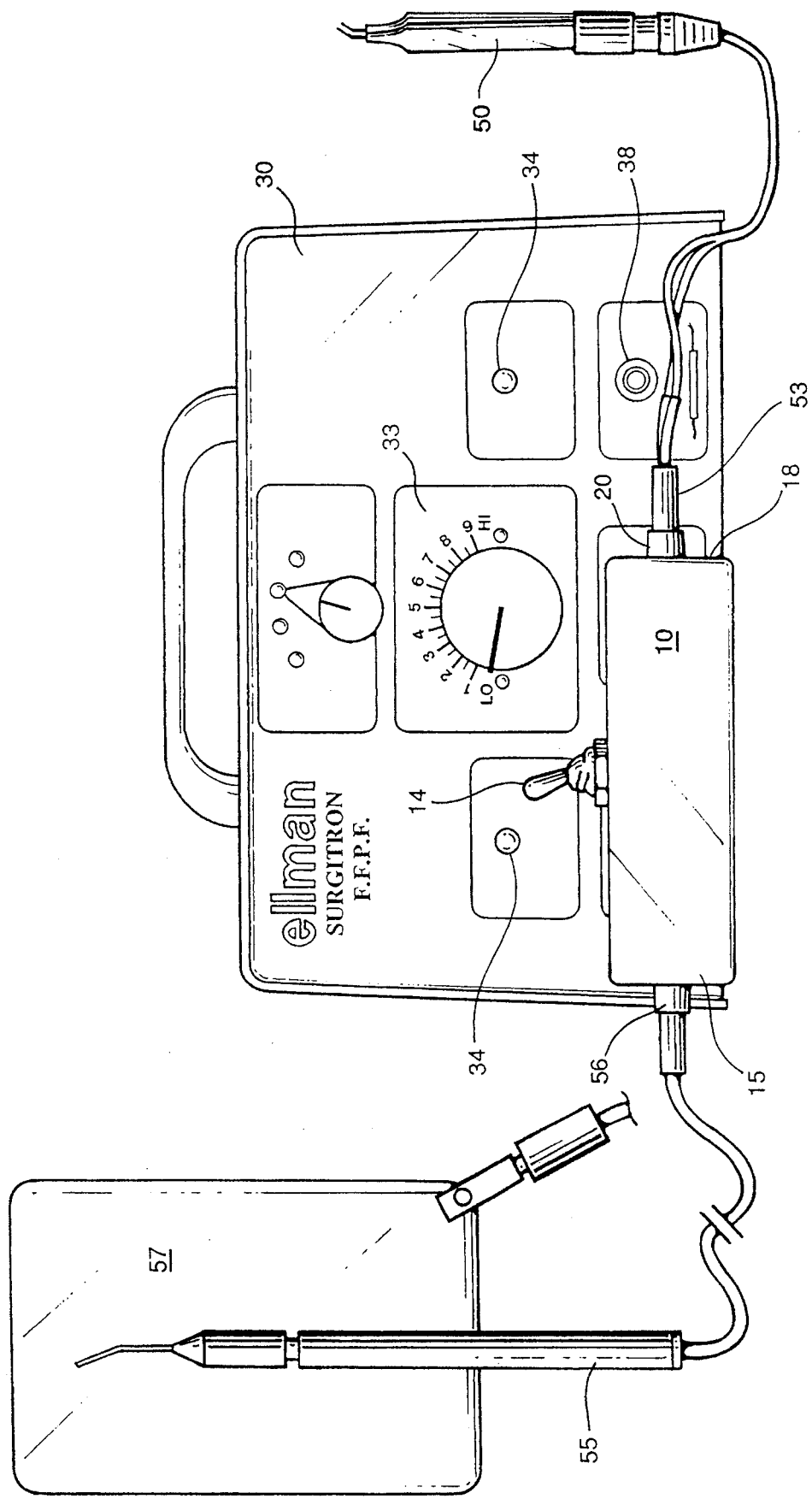
FIG. 4 is a front view showing the adaptor of FIG. 1 plugged into the front panel of the instrument of FIG. 2.

In accordance with the invention, the adaptor 10 is plugged into the front panel of the electrosurgical instrument 30 by engaging the two banana plugs 22, 23 on the adaptor to the ground plate and handpiece connectors 36, 37 of the instrument. This is illustrated at 40 in FIG. 3. The lateral spacing of the two banana plugs 22, 23 matches the lateral spacing of the two connectors 36, 37 making it very easy to plug the adaptor 10 directly into the connectors on the instrument. FIG. 4 shows the adaptor 10 plugged into the front panel of the instrument 30. FIGS. 3 and 4 also show a bipolar forceps 50 whose male banana plugs 52, 53 are plugged into the female connectors 19, 20 on the right side 18 of the adaptor, and a ground plate 57 and handpiece 55 are plugged, respectively, into the female connectors 16, 17 at the left side 15 of the adaptor 10.

Figure 5:
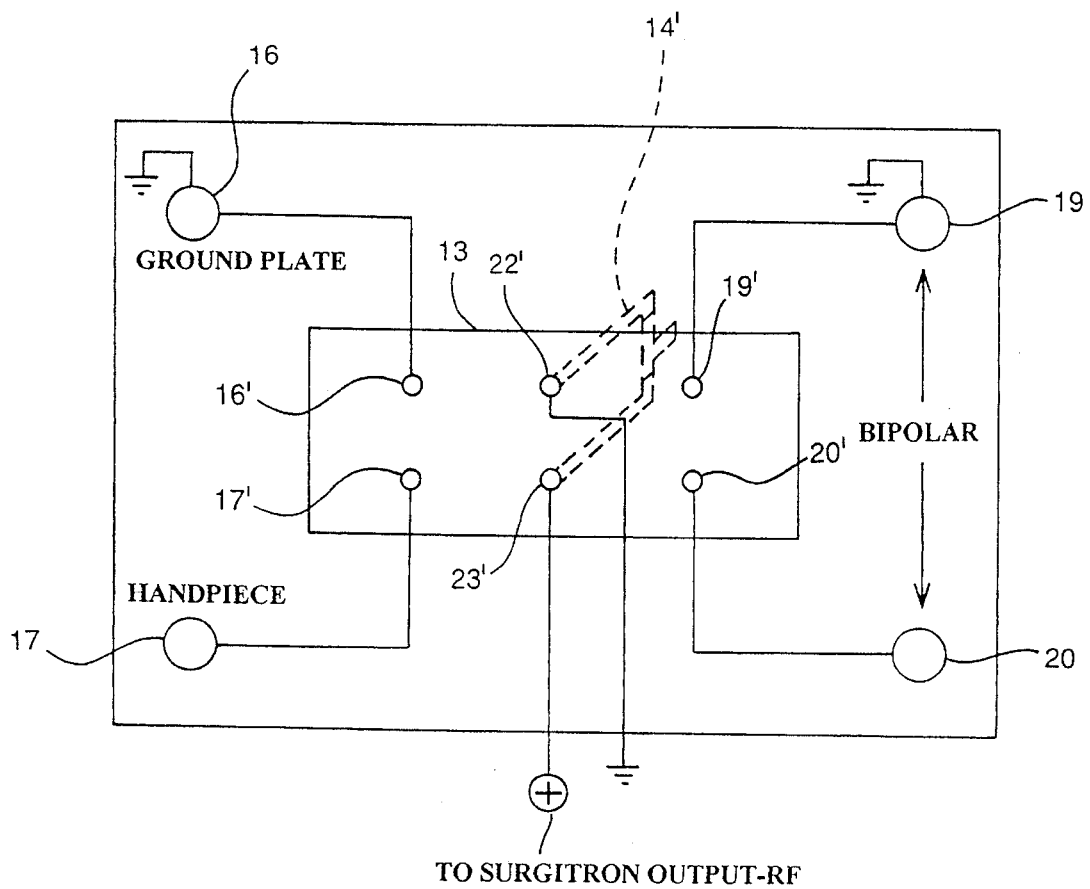
FIG. 5 is a circuit schematic of one form of electrical circuit for the adaptor of FIG. 1.

The operation will be clear from the circuit schematic of the adaptor 10 shown in FIG. 5. Essentially, a double-pole, double-throw switch 13 with the terminals on the switch referenced by primed numbers coresponding to the connectors on the adaptor. Thus, the center terminals 22' and 23' are connected, respectively, to the plugs 22, 23, which plug, respectively, into the ground plate socket 36 and handpiece socket 37; the right terminals 19' and 20' are connected, respectively, to the sockets 19, 20; and the left terminals 16' and 17' are connected, respectively, to the sockets 16, 17. The switch handle is shown in phantom at 14'. When thrown into a first position, its left position, it connects terminal 23' to terminal 17' and terminal 22' to terminal 16', and when thrown into a second position, its right position, it connects terminal 23' to terminal 20' and terminal 22' to terminal 19'. When in the first position, when the electrosurgical instrument is energized, RF power is fed to the socket 17 and to the handpiece when plugged into that socket. The ground plate 57 when plugged into the socket 16 is then attached to the patient, and the surgeon can perform any desired unipolar electrosurgical procedure. When the switch is thrown into its second position, then RF power and ground are, respectively, applied to the sockets 20, 19 and a bipolar forceps 50 plugged into those sockets will be active and capable of performing a coagulation procedure.

The adaptor of the invention offers the advantages of accessibility, immobility, and versatility: accessibility, as the user is able to reach and exercise the switch function without touching anything else, simplifying greatly maintaining sterile fields; immobility, as the adaptor will be firmly anchored and thus immovable and steadfast when plugged into the instrument while the function switch 14 is thrown back and forth; versatility, as the adjustability from one electrosurgical mode to another mode is extremely simple; unplugging cables and plugging in different cables becomes unnecessary. A further advantage is that plugging the adaptor directly into the RF power source not only provides immobility but also avoids the need for cables. Still another advantage is that the two electrodes, unipolar and bipolar, are located at opposite ends of the adaptor box 11 with ample room for clear labelling and color coding if desired to avoid confusing the two electrosurgical modes. Finally, the switch handle is prominent and easily manipulated without having to touch any of the cabling.

In the preferred mode of operation, the RF power is in a frequency range exceeding 2 MHz, 3.8 MHz being preferred. However, the invention is not so limited and other frequency ranges for electrosurgical procedures are also considered within the scope of the invention.

It will be understood that the invention is not limited to the specific connectors shown. While banana connectors are preferred, other connectors that would firmly hold together when engaged can be substituted. Also, different shapes of the housing are also considered within the scope of the invention so long as the shape allows for widely-spaced female connectors for receiving the unipolar handpiece and bipolar forceps cable connectors, and that allows sufficient room for the switch handle that will allow a user to operate the switch without touching the cabling.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An adaptor for connection to electrosurgical apparatus and for selectively providing power to operate a unipolar handpiece and a bipolar forceps, said adaptor comprising:

(a) a housing, (b) a double-pole, double-throw switch within the housing, said switch having an operating handle protruding from a side of the housing, said switch having a first pair and a second pair of terminals and a set of common terminals for selective connection to the first terminals when the switch handle is in a first position and to the second terminals when the switch handle is in a second position, (c) first electrical connectors at a side of the housing for receiving connectors of a unipolar handpiece and of a ground plate, said first connectors being connected to the first pair of terminals of the switch, (d) second electrical connectors at a side of the housing for receiving connectors of a bipolar forceps, said second connectors being connected to the second pair of terminals of the switch, (e) third electrical connectors at a side of the housing for respectively engaging a fourth connector providing RF electrosurgical currents and a fifth connector providing electrical ground, said third connectors being respectively connected to the set of common terminals of the switch.

2. An adaptor according to claim 1, wherein the third connectors are firmly anchored at a side of the housing such that the third connectors are engageable to the fourth and fifth connectors by plugging the housing via its third connectors into the fourth and fifth connectors.

3. An adaptor according to claim 1, wherein all the connectors are banana-type connectors.

4. An adaptor for connection to electrosurgical apparatus and for selectively providing power to operate a unipolar handpiece and a bipolar forceps, said adaptor comprising:

(a) a housing, (b) a double-pole, double-throw switch within the housing, said switch having an operating handle protruding from a first side of the housing, said switch having a first pair and a second pair of terminals and a set of common terminals for selective connection to the first terminals when the switch handle is in a first position and to the second terminals when the switch handle is in a second position, (c) first electrical connectors at a second side of the housing for receiving connectors of a unipolar handpiece and of a ground plate, said first connectors being connected to the first pair of terminals of the switch, (d) second electrical connectors at a third side of the housing for receiving connectors of a bipolar forceps, said second connectors being connected to the second pair of terminals of the switch, (e) third electrical connectors at a fourth side of the housing for respectively engaging a fourth connector on the electrosurgical apparatus providing RF electrosurgical currents and a fifth connector on the electrosurgical apparatus providing electrical ground, said third connectors being respectively connected to the set of common terminals of the switch.

5. An adaptor according to claim 4, wherein the first and second connectors are female connectors, and the third connectors are male connectors.

6. An adaptor according to claim 5, wherein the third connectors are firmly anchored to the fourth side of the housing whereby the adaptor as a whole can be plugged into the fourth and fifth connectors on the electrosurgical apparatus.

7. In combination:

an electrosurgical apparatus having a housing with a front panel and on the front panel an RF female connector supplying RF power and an electrical ground female connector when the electrosurgical apparatus is enegized;

an adaptor for connection to the electrosurgical apparatus and for selectively providing power to operate a unipolar handpiece and a bipolar forceps;

said adaptor comprising:

(a) an adaptor housing, (b) a double-pole, double-throw switch within the adaptor housing, said switch having an operating handle protruding from a first side of the adaptor housing, said switch having a first pair and a second pair of terminals and a set of common terminals for selective connection to the first terminals when the switch handle is in a first position and to the second terminals when the switch handle is in a second position, (c) first electrical connectors at a second side of the adaptor housing for receiving connectors of a unipolar handpiece and of a ground plate, said first connectors being connected to the first pair of terminals of the switch, (d) second electrical connectors at a third side of the adaptor housing for receiving connectors of a bipolar forceps, said second connectors being connected to the second pair of terminals of the switch, (e) third electrical connectors at a fourth side of the adaptor housing for respectively engaging the RF connector on the electrosurgical apparatus front panel for providing RF electrosurgical currents and the ground connector on the electrosurgical apparatus front panel providing electrical ground, said third connectors being respectively connected to the set of common terminals of the switch.

8. The combination according to claim 7, wherein the first and second connectors are female connectors, and the third connectors are male connectors.

9. The combination according to claim 8, wherein the third connectors are firmly anchored to the fourth side of the housing whereby the adaptor as a whole can be plugged into the connectors on the front panel of the electrosurgical apparatus.

10. The combination according to claim 7, further comprising an electrosurgical handpiece with a connector for engaging one of the first connectors, a ground plate with a connector for engaging another of the first connectors, and a bipolar forceps with twin connectors for engaging the second connectors.

* * * * *